(12) United States Patent     (10) Patent No.: US 9,301,680 B2
Fassi et al.     (45) Date of Patent: Apr. 5, 2016

(54) DEVICE FOR MONITORING POSITION AND MOVEMENTS OF AN EYE, PARTICULARLY SUITABLE FOR OCULAR RADIOTHERAPY

(71) Applicant: POLITECNICO DI MILANO, Milan (IT)

(72) Inventors: Aurora Fassi, Vanzaghello (IT); Marco Riboldi, Milan (IT); Christian Fabio Forlani, Milan (IT); Guido Baroni, Monza (IT)

(73) Assignee: POLITECNICO DI MILANO (IT)

( * ) Notice: Subject to any disclaimer, the term of this patent is extended or adjusted under 35 U.S.C. 154(b) by 162 days.

(21) Appl. No.: 14/353,996

(22) PCT Filed: Oct. 31, 2012

(86) PCT No.: PCT/IB2012/056056
§ 371 (c)(1),
(2) Date: Apr. 24, 2014

(87) PCT Pub. No.: WO2013/064999
PCT Pub. Date: May 10, 2013

(65) Prior Publication Data
US 2014/0300867 A1    Oct. 9, 2014

(30) Foreign Application Priority Data
Nov. 2, 2011 (IT) .............................. VR2011A0201

(51) Int. Cl.
*A61B 3/14* (2006.01)
*A61B 3/10* (2006.01)
*A61B 3/02* (2006.01)
*A61B 3/113* (2006.01)
(Continued)

(52) U.S. Cl.
CPC ............... *A61B 3/113* (2013.01); *A61B 3/0025* (2013.01); *A61N 5/1017* (2013.01);
(Continued)

(58) Field of Classification Search
USPC ......... 351/200, 203–206, 209–212, 221, 222, 351/243–246; 600/318, 356, 383, 558
See application file for complete search history.

(56) References Cited

U.S. PATENT DOCUMENTS 4,848,340 A    7/1989    Bille et al.
6,152,563 A    11/2000    Hutchinson et al.
(Continued)

FOREIGN PATENT DOCUMENTS

WO    WO 2011/124852 A1    10/2011

OTHER PUBLICATIONS

International Search Report dated Mar. 7 2013 issued in corresponding International patent application No. PCT/IB2012/056056.

*Primary Examiner* — Joseph P Martinez
*Assistant Examiner* — Brandi Thomas
(74) *Attorney, Agent, or Firm* — Ostrolenk Faber LLP

(57) ABSTRACT

A device for non-invasive monitoring of an eye position and ocular movements of a patient having: a housing body (2) having at least one through opening (2a); a plurality of light sources (3) housed in said housing body (2); a plurality of sensor means (4) housed in said housing body (2); deflector means (6) for invisible radiation (RL) supplied, in use, by said plurality of light sources (3) and reflected by said eye (O) under examination; support means (8) that can be adjusted for said housing body (2); at least one program data processing and control unit (9). The support means (8) can be adjusted in such a way that the through opening (2a) of the housing body (2) can be placed at the eye (O) under examination so that the invisible radiation hits the eye (O) frontally. The program data processing and control unit (9) is designed to calculate instant-by-instant the position and orientation of a suitable three-dimensional reference system integral with the eye with respect to a predetermined three-dimensional reference system.

24 Claims, 9 Drawing Sheets

(51) Int. Cl.
*A61N 5/10* (2006.01)
*A61B 3/00* (2006.01)
*G06K 9/00* (2006.01)
*A61F 9/008* (2006.01)

(52) U.S. Cl.
CPC .. *G06K 9/00604* (2013.01); *A61F 2009/00846* (2013.01); *A61N 2005/1087* (2013.01); *A61N 2005/1091* (2013.01)

(56) References Cited

U.S. PATENT DOCUMENTS

| | | |
|---|---|---|
| 6,159,202 A | 12/2000 | Sumiya et al. |
| 6,626,537 B1 * | 9/2003 | Odom et al. ............ 351/205 |
| 2009/0163898 A1 | 6/2009 | Gertner et al. |
| 2010/0254513 A1 | 10/2010 | Gertner |

* cited by examiner

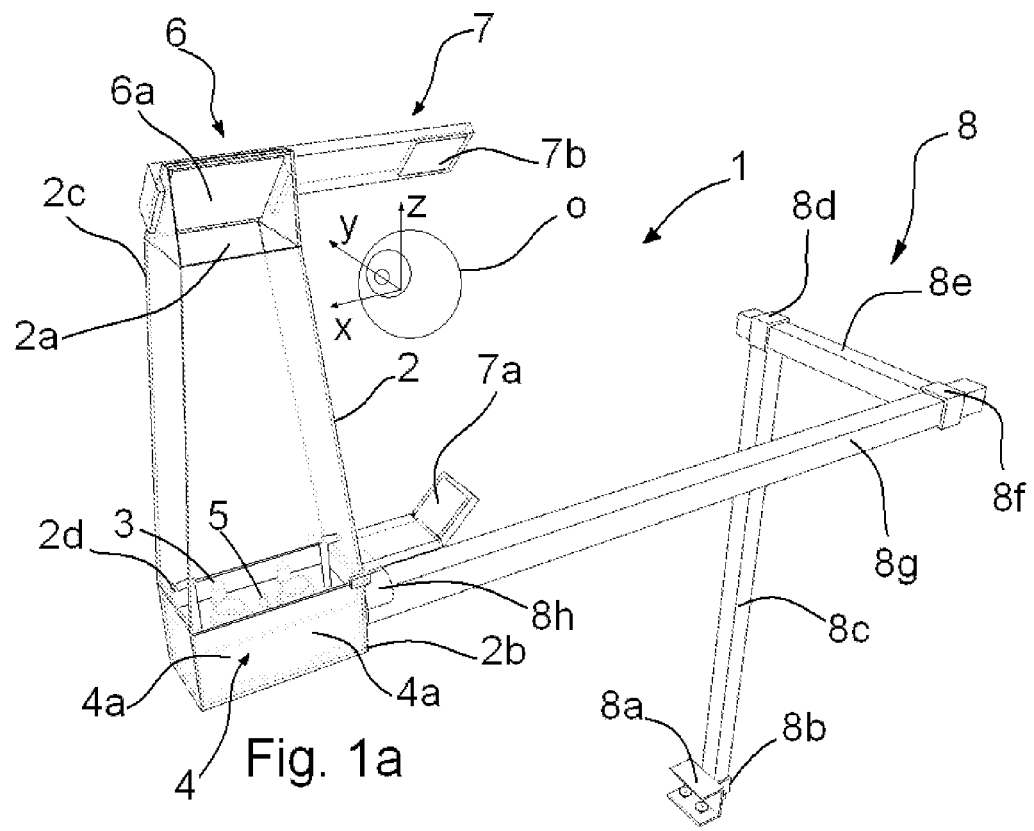

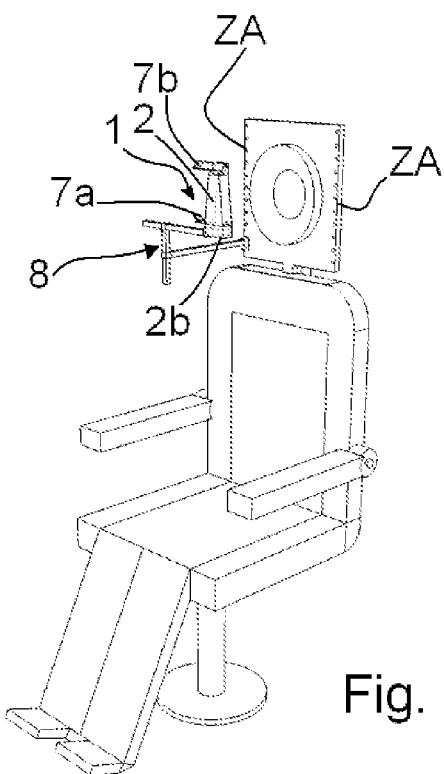
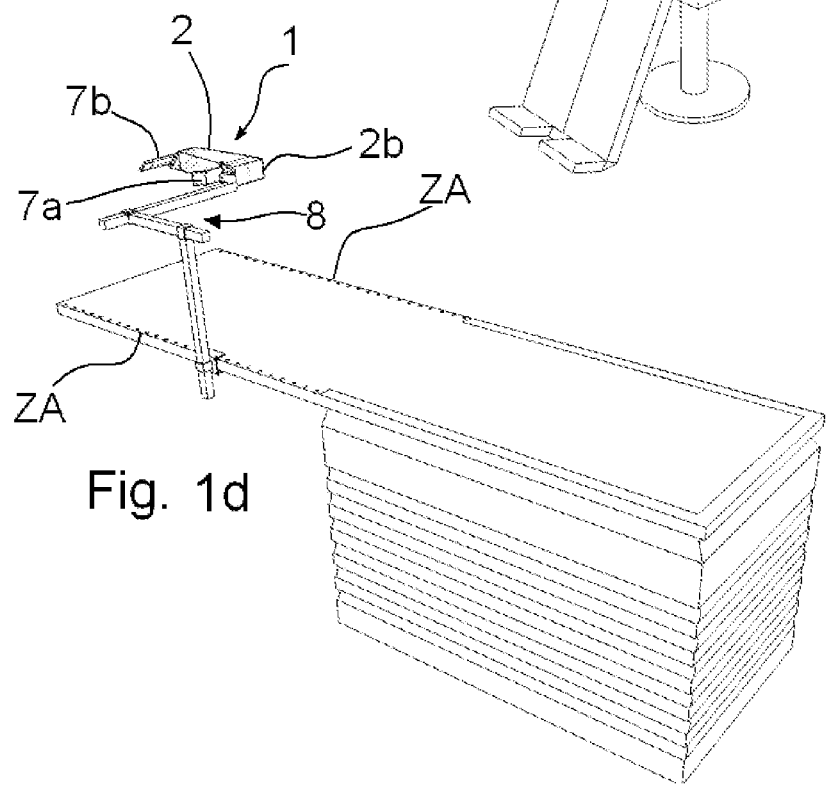

DEVICE FOR MONITORING POSITION AND MOVEMENTS OF AN EYE, PARTICULARLY SUITABLE FOR OCULAR RADIOTHERAPY

CROSS REFERENCE TO RELATED APPLICATIONS

The present application is a 35 U.S.C. §371 National Phase conversion of PCT/IB2012/056056, filed Oct. 31, 2012, which claims benefit of Italian Application No. VR2011A000201, filed Nov. 2, 2011, the disclosure of which is incorporated herein by reference. The PCT International Application was published in the English language.

TECHNICAL FIELD OF THE INVENTION

The present invention regards a non-invasive device for the automatic monitoring of the ocular position and movements of a patient. More particularly, the invention relates to a device particularly suitable in external band radiotherapy treatments of ocular tumors, typically by means of proton therapy and/or stereotactic photon radiotherapy.

BACKGROUND OF THE INVENTION

The introduction of radiotherapy has represented a considerable step forward in the treatment of intraocular tumors, substituting the radical operation of the eye enucleation. Preservative radiotherapy treatments indeed allow preserving the integrity of the eye and maintaining its residual visual capacity, without compromising the survival of the patient and without the onset of secondary metastasis.

Proton therapy is considered the treatment of choice for ocular tumors due to the extreme spatial selectivity and to the advantageous modes for supplying the treatment. Proton beams indeed allow obtaining a spatial distribution of the radiation dose highly in accordance with the volume to be treated, which in the case of ocular pathologies can have very reduced size, even equal to a few millimeters. In addition, ocular tumors are often localized in the rear pole of the eye, near very sensitive structures such as the optical disc and the fovea; due to the high dose gradients, proton therapy treatments allow completely saving as much as possible the critical ocular structures, thereby maintaining the patient's visual capacities intact.

In addition to proton therapy, one of the most widespread radiotherapy techniques for the treatment of ocular tumors is stereotactic photon radiotherapy. Stereotactic radiotherapy employs multiple, focused high-energy photon beams with high geometric precision on the tumor region to be treated. Such technique allows obtaining very high dose gradients, thus limiting the irradiation of the surrounding healthy tissues.

The therapeutic effectiveness and quality of such treatments are closely related to the accuracy of the localization of the ocular lesion and to the compensation of the eye movements, which a patient may make even involuntarily during administration of radiation.

Clearly, it is critical to evaluate with high precision, during the planning step of a treatment, the distribution in the eye of the ocular tissues to the treated, and during the treatment, i.e. during the administration of a radiation dose, the position of the patient's eye with respect to the incident radiation beam. Such evaluation is important for allowing the irradiation of only the tissues to be treated, and therefore avoiding the irradiation of healthy eye tissues, so as to maintain as much as possible the visual capacity of the patient subjected to treatment.

For this purpose, over the years various control systems have been proposed, both of invasive and non-invasive type, aimed to detect the ocular position and the ocular movements during a treatment session. For example, systems have been proposed that provide for the invasive application of radiopaque clips to the margins of the treatment zone (e.g. tumor zone) for the indirect localization of the lesion by means of multiple radiographs of the eye.

Alternatively, systems for automatically controlling ocular movements have been proposed, which are based on monitoring the eye position starting from two-dimensional images acquired by a telecamera; such images contain specific ocular reflections obtained with the use of infrared sources directed towards the eye under examination.

Some of the conventional equipment provide that the administration of the radiation dose is manually interrupted if there are ocular movements by the patient under treatment, even involuntary ones. Such movements are evaluated in a qualitative manner by the doctor, typically by observing on a monitor the deviations of the eye with respect to pre-established reference borders; or they can be automatically evaluated, e.g. by estimating the eye rotation degree, starting from the pupil borders identified on the ocular images acquired by a control system as mentioned above.

In patent application US-2010/0254513, for example, a device is taught that allows bringing a reference axis (typically the optical axis) of the patient's eye into alignment with the treatment system, also by means of the use of invasive means.

In patent application US-2009/0163898, on the other hand, a telecamera and a light source are used, focused on the eye to be treated in order to identify a reference ocular axis. In particular, the reference ocular axis is that at which the center of the limbus identified on the images acquired with the telecamera coincides with a corneal reflection generated by the light source.

Patent application US-2009/0182311 teaches an equipment and a method of obtaining the alignment and stabilization of the ocular position by means of a contact lens applied to the ocular surface. The lens is connected to an articulated arm which allows positioning and aligning the eye with respect to a treatment equipment. The equipment also includes a telecamera used for verifying the centering of the contact lens with the center of the limbus and for monitoring possible movements of the eye with respect to the lens. Localizing the contact lens by means of specific sensors (radio transmitters or laser pointers), allows to find the 3D position and the orientation of the eye in a reference system outside the eye itself.

In patent application US-2009/0161826 the use of a standardized model of the human eye is described, which model is adapted to the specific patient based on the biometric parameters obtained by specific imaging techniques (funduscopy, optical tomography, MRI, etc.). The ocular model thus obtained is processed and (as the position is known of the contact lens applied on the eye to be treated) it allows determining the three-dimensional position of the ocular structures of interest (macula, optical disc, etc.) in an external reference coordinate system. This solution also allows establishing, before treatment, the amplitude and duration of the ocular movements allowed to the patient, in order to maintain the radiation dose at the critical optical structures below a certain level.

There are numerous drawbacks of such conventional systems. Some systems, as mentioned above, are invasive systems and provide for the use of auxiliary means such as contact lenses or radiopaque clips, whose application certainly causes discomfort in patients. Other systems, even if they are non-invasive, do not supply any information on the position, in a three-dimensional reference system, of the ocular lesion and the ocular structures at risk and provide for the manual interruption of the treatment based on a qualitative estimation of the ocular movements. Moreover, the treatment systems based on proton therapy, before starting the treatment procedure, require long and laborious invasive procedures for positioning the patient in order to determine the ocular region to be treated and to arrange such a region in the field of action of the radiant beam (treatment isocenter), so as to only hit the damaged zone and not the surrounding healthy tissues of the eye to be treated.

Not least, several of the abovementioned systems are standardized, in the sense that they do not provide for the personalization of the treatment system on the single patient; they require the use of fixed and isotropic thresholds on the ocular movements and the use of standardized models of the ocular structure, which thresholds and models are not "adaptable" or are adaptable to a very limited extent, often inadequate for the specific ocular morphology of the patient to be subjected to the treatment.

SUMMARY OF INVENTION

The main object of the present invention is to provide a device for monitoring the eye position and ocular movements of a patient that is non-invasive and which allows a precise evaluation of the position of an eye, of the respective structures of interest, the ocular lesion included, with respect to a predetermined three-dimensional reference system.

The term "predetermined three-dimensional reference system", in the present description and claims, refers to a three-dimensional reference system according to which the measures in output form the device according to the present invention are expressed. A "predetermined three-dimensional reference system" can be, for example, an absolute reference system integral with a room wherein the device according to the present invention is placed. In the case the device according to the present invention is combined with an equipment for planning the therapeutic treatment comprising, for example an equipment for acquiring CAT/MRI images, or is combined with an equipment for delivery of treatment dose, an example of a "predetermined three-dimensional reference system" is a reference system integral with such equipment for acquisition of CAT/MRI images or such equipment for delivery of the treatment dose, respectively.

Another object of the present invention is to provide a device for non-invasive monitoring the eye position and ocular movements of a patient, with respect to a predetermined three-dimensional reference system, whose functioning is based on the specific ocular morphology of the patient himself.

Another object of the present invention is to provide a device for non-invasive monitoring the eye position and ocular movements of a patient, with respect to a predetermined three-dimensional reference system, such device being particularly easy and simple to use during the steps of planning and execution of a radiotherapy treatment.

Another object of the present invention is to provide a device for non-invasive monitoring the eye position and ocular movements of a patient, with respect to a predetermined three-dimensional reference system, which has reduced size with respect to conventional equipment.

Still another object of the present invention is to provide a device for non-invasive monitoring the eye position and ocular movements, with respect to a predetermined three-dimensional reference system, which can be obtained at competitive costs.

A further object of the present invention is to provide a device for non-invasive monitoring of the eye position and ocular movements, with respect to a predetermined three-dimensional reference system, which is compatible with other diagnostic instrumentation and can be easily integrated with specific equipment for planning and executing radiotherapy ocular treatments.

Not least object of the present invention is to provide a method of non-invasive monitoring of the ocular movements of a patient, with respect to a predetermined three-dimensional reference system, which is practical to execute and has high precision and reliability.

According to a first aspect of the present invention, a device for non-invasive monitoring of the position and ocular movements of an eye of a patient, comprising:

a housing body having at least one through opening;

a plurality of light sources located in said housing body and suitable for emitting invisible radiation through said at least one through opening;

a plurality of sensor means housed in said housing body and secured thereto and to said plurality of light sources, said plurality of sensor means being designed to detect said invisible radiation emitted, in use, by said plurality of light sources outside said housing body and reflected by the eye under examination, and convert said detected invisible radiation into a suitable electrical signal;

deflector means for said invisible radiation emitted, in use, by said plurality of light sources and reflected by said eye under examination, the deflector means being supported by said housing body at said at least one through opening;

adjustable support means for said housing body;

at least one program data processing and control unit electrically connected to said plurality of light sources, to said plurality of sensor means and to said support means, and designed to send/receive suitable control signals to/from said plurality of light sources, to/from said plurality of sensor means and to/from said support means and to process said electrical signal correlated with the invisible radiation detected by said plurality of sensor means, characterized in that said support means are adjustable in such a way that said through opening of said housing body is placeable at said eye (O) under examination whereby said invisible radiation hit said eye frontally and in that the at least one program data processing control and unit is designed to calculate instant-by-instant the position and orientation of a suitable three-dimensional reference system integral with the eye, with respect to a predetermined three-dimensional reference system.

According to a further aspect of the present invention, a method is provided of non-invasive monitoring of the position of an eye and of ocular movements of a patient, with respect to a predetermined three-dimensional reference system, comprising the following operative steps:

arranging a device according to the first aspect of the present invention so that the invisible radiations delivered by said plurality of light sources frontally hit, in use, an eye to be examined;

emitting said invisible radiations towards said eye;

acquiring of at least a plurality of images encoded in suitable electrical signals by means of said data processing and control unit;

processing said electric signals by said data processing and control unit; and calculating, on the base of said processing by said data processing and control unit, the position and orientation of a reference system integral with said eye under examination with respect to said predetermined three-dimensional reference system.

BRIEF DESCRIPTION OF THE DRAWINGS

Further aspects and advantages of the present invention will be clearer from the following detailed description of several currently preferred embodiments thereof, given as merely exemplifying and non-limiting in the drawing set, wherein:

FIG. 1a shows a perspective view of a device for monitoring ocular movements according to the present invention;

FIG. 1b illustrates a detail of the device for monitoring ocular movements according to the present invention;

FIGS. 1c and 1d each show a perspective view, in reduced scale, of the device of FIG. 1a mounted on a treatment chair or bed, respectively;

FIG. 2 illustrates a block diagram of the components of the monitoring device of FIG. 1a;

DESCRIPTION OF PREFERRED EMBODIMENTS

Figure 2:
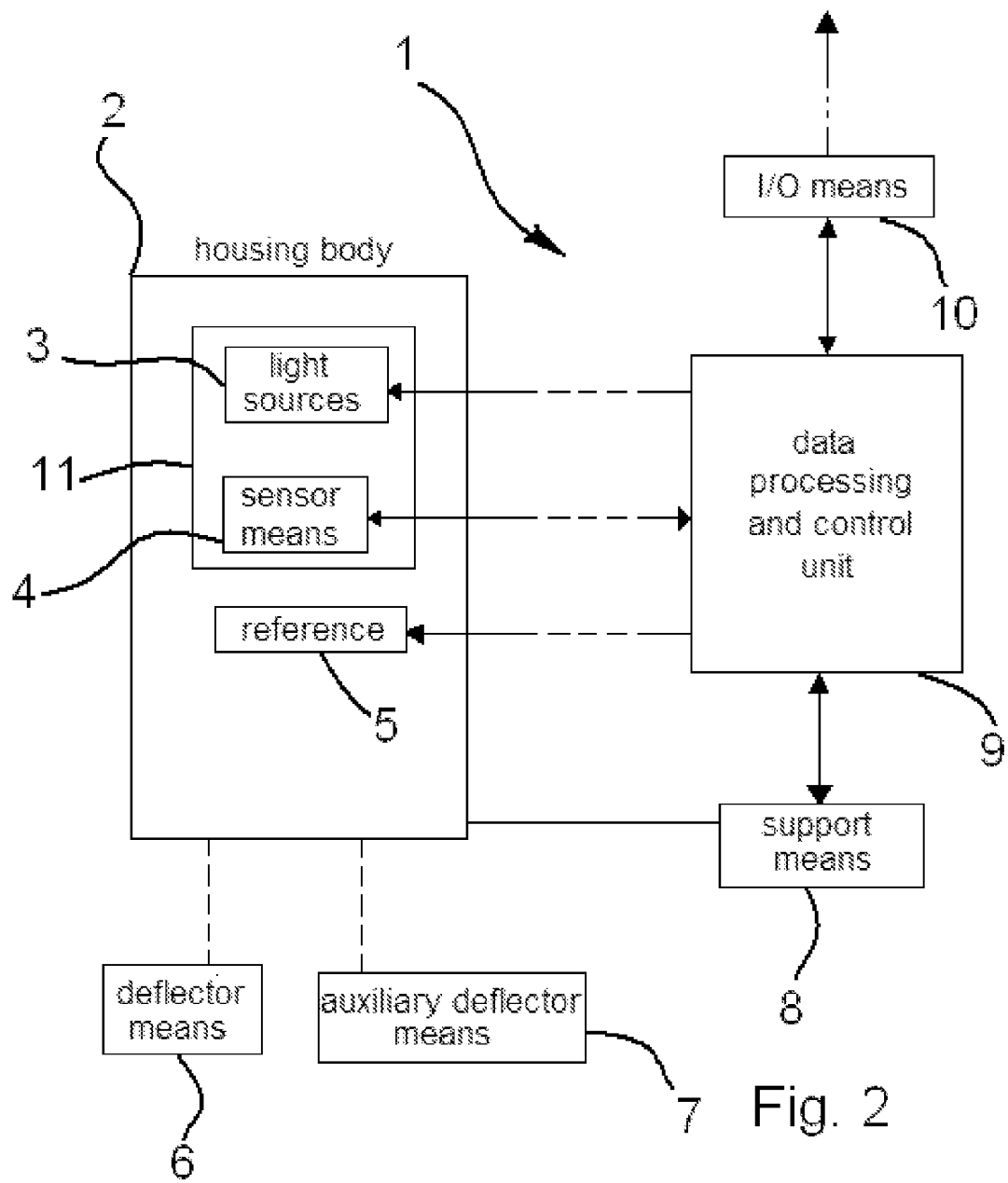

In the accompanying drawing, equivalent or similar parts or components were given the same reference numerals.

In the present description and in the claims:

with the term "transverse plane" of the eye under examination, it is intended the plane of the eye comprising the reference axes x-z of a reference system x-y-z having as origin the center of the cornea of the eye, as illustrated in FIG. 1a;

with the term "longitudinal plane" of the eye, it is intended the plane of the eye comprising the reference axes y-z of the reference system x-y-z of FIG. 1a; and with the term "sagittal plane" of the eye, it is intended the plane of the eye comprising the reference axes x-y of the reference system x-y-z of FIG. 1a.

With reference first to FIGS. 1a, 1b, 1c, 1d and 2, it is observed that a device for monitoring the ocular movements according to the present invention, is marked by the reference numeral 1, and comprises a housing body or casing 2 with box-like configuration (for example), in which a plurality of light sources 3 and sensor means 4 are housed.

Advantageously, the housing body 2 has a substantially elongated configuration and comprises two opposite ends, one distal in use 2b and another proximal or supply 2c, in use. More particularly, the light sources 3 and the sensor means 4 are rigidly anchored to each other and to the housing body 2 at the distal end and are directed toward or face the supply end 2c of the casing 2, which supply end is opposite to the distal end 2b.

The housing body 2 has a through opening 2a, typically at its proximal or supply ends 2c, provided for the passage of light radiation or rays RL suppliable by the plurality of light sources 3; in use, such radiation is designed to hit an eye O under examination, which eye is placed across from and in alignment with the opening 2a. The opening 2a also allows the entrance in the housing body 2 of part of the light radiation RL emitted by the light sources 3 and (in use) reflected by the eye O, and designed to hit the sensor means 4.

The plurality of light sources 3 preferably comprises two infrared light sources (IR), more particularly two infrared light emitting diodes (or LEDs) of any suitable type. The sensor means 4 preferably comprise a pair of miniaturized stereoscopic telecameras 4a with high spatial and temporal resolution of any suitable type, which are particularly sensitive to infrared radiation and are designed to acquire images of the eye O hit by the radiation RL.

The device according to the present invention also comprises a reference means 5, e.g. a red visible light LED, anchored or fixed at the sensor means 4, preferably between two stereoscopic telecameras 4a, and intended to emit a light radiation that the eye O of a patient under examination will have to stare at, so as to obtain the stabilization of his gaze direction.

It will be observed that the particular elongated configuration of the housing body 2 and the anchorage, to the distal end 2b thereof, of the light sources 3, the sensor means 4, and the reference means 5, allow having, in use, such light sources 3, sensor means 4, and reference means 5, at a sufficient distance from the through opening 2a of the device according to the present invention. At the through opening 2a of the device, there is, in use, the eye of the patient, and, therefore, the treatment zone; such a zone (as will be explained below) is usually affected by ionizing radiation or magnetic fields, which can cause alterations in the functioning of the light sources 3, sensor means 4, and reference means 5. The moving away of the aforesaid components from the eye also allows avoiding alterations of the CAT/MRI images, which can be acquired during planning of treatment, and undesired dose absorption of treatment dose during the treatment itself.

The device 1 also comprises deflector means 6 for the light radiation RL both leaving and entering the housing body 2, which are advantageously provided for allowing the irradiation of the eye O of the patient while maintaining the sensitive components of the device (sensor means 4, light sources 3 and the reference means 5) at a sufficient distance from the eye itself, and hence at a sufficient distance, in use, from the treatment zone or range. The deflector means 6 advantageously comprise a mirror 6a arranged at the opening 2a of the housing body 2, according to an angle with respect to the sagittal plane of the eye O under examination, such that the light radiation RL reflected by the mirror 6a travels along a direction substantially parallel to the sagittal plane of the eye itself.

The deflector means 6 also comprise auxiliary deflectors 7, which are provided in the case in which the eye O under examination has reduced visual capacities and hence it cannot correctly fixate the reference means 5 in order to obtain the gaze stabilization. The auxiliary deflector means 7 comprise a couple of mirrors, a lower 7a and an upper 7b mirror, suitably arranged with respect to the other eye of the patient, in a manner so as to send the visible light emitted by the reference means 5 over such eye, always along a direction substantially parallel to the sagittal plane of the eye.

For this purpose, the device 1 according to the present invention also has, on two opposite lateral faces of the housing body 2, a respective through hole or auxiliary through opening 2d through which a visible reference light (always emitted by the reference means 5) is transmitted in any suitable manner, e.g. by means of an optical fiber; such light first hits mirror 7a, then mirror 7b and finally the eye O of the patient.

It will be understood that the auxiliary deflector means 7 can be applied at one or the other of the two lateral opposite sides of the housing body 2, in which a respective through hole or auxiliary through opening 2d is provided, the side depending on whether the eye O under examination is the left or the right eye. Of course, the eye under examination O must always remain correctly situated at the through opening 2a.

In FIG. 1a, the eye O under examination is illustrated as an example, arranged in proximity to the device 1 and the deflector means of the infrared radiation, which comprise a mirror 6a arranged at 45° with respect to the sagittal plane of the eye. The auxiliary deflector means instead provide for a lower mirror 7a arranged at 45° with respect to the longitudinal plane of the eye under examination and an upper mirror 7b arranged like the mirror 6a, at 45° with respect to the sagittal plane of the eye O.

The device 1 according to the present invention is advantageously fixable to a support means 8 that can be adjusted manually and/or on command for the preferably removable anchorage to a treatment bed or chair, as illustrated in FIGS. 1c and 1d. The support means 8 is, for example, constituted by a robotic manipulator with at least five (5) degrees of freedom, obtained by means of rotational joints and/or prismatic joints coupled to servomotors in any one suitable manner, as is known at the state of the art. More particularly, the support means 8 comprise means 8a for anchoring to a treatment chair or bed, e.g. configured as a C-shaped bracket that is removably fixable, e.g. boltable, to a chair or a bed at an anchorage edge ZA thereof. The anchorage bracket 8a also has a reception and guide collar or sleeve 8b.

The support means 8 also comprise a substantially rigid first arm 8c preferably having a polygonal cross section, e.g. square cross section, with one end slidably housable in the collar or sleeve 8b, the collar or sleeve 8b preferably having configured opening corresponding to the external surface of the arm 8c. The arm 8c extends in a first direction and at the other end thereof has, in turn, a reception and guide collar or sleeve 8d, in which guide collar or sleeve 8d one end of a substantially rigid second arm 8e is slidably housable, such second arm 8e extending in a second direction that is preferably orthogonal to the first arm 8c. The second arm 8e in turn terminates at the other end thereof with a reception and guide collar or sleeve 8f, in which one end of a third support arm 8g is slidably housable, such arm 8g extending in a third direction, preferably perpendicular to the second arm 8e. The third arm 8g is slidably mounted in the collar 8f of the arm 8e and has the other end thereof engaged by an angular movement group 8h, fixed in any one suitable way to the housing body or casing 2 of the device 1 and set to make the arm 8g move angularly around its own longitudinal axis, i.e. with two degrees of freedom.

If desired, the various reception and guide collars or sleeves 8b, 8d and 8f can also be equipped with screws for fixing in position (not illustrated in the drawings and possibly associated with a control switch) for the respective arm 8c, 8e and 8g.

It will be observed that the aforesaid support means 8, which can be adjusted manually and/or on command, can also be obtained in any other suitable manner, provided that the position and orientation of such support means 8 in the predetermined three-dimensional reference system and, accordingly, that of the device 1 according to the present invention supported by said support means, can be easily reproduced in time for a given patient, with errors with respect to the position and orientation previously obtained, in the predetermined three-dimensional reference system, around od less than 0.5 mm and 0.1°. For example, the support means could be obtained by using only rotational joints.

With such a configuration of the support means 8, it is possible to arrange, in use, the device 1 according to the present invention in a way such that the through opening 2a of the housing body 2 is in correct correspondence with the eye O under examination and that the light radiation RL emitted by the light sources 3 hits the eye O frontally, according to a direction parallel to the sagittal plane of the eye itself.

The monitoring device 1 according to the present invention also comprises a data processing and control unit 9 (FIG. 2), e.g. a remote one, of any suitable type, which unit is set to control the activation/deactivation of the light sources 3, of the sensor means 4, of the reference means 5, as well as the movement of the support means 8 (if it occurs on command) electrically connected thereto, by sending suitable electrical control signals. The data processing and control unit 9 also receives, in input from the support means 8, suitable control signals (relative to the mutual positions of all its sections); it also receives, from the sensor means 4, the images of the eye O under examination acquired by the sensor means and encoded into suitable electrical signals.

The data processing and control unit 9 is electrically connected to input-output means 10, of any one suitable type, e.g. a USB port or a network cable, which allow sending the data processed by the unit 9 to other systems and/or equipment; such systems will be described below, and they can comprise, among other things, an equipment for planning the treatment for the eye O and an equipment for administration of a treatment dose.

The monitoring device 1 according to the present invention can be advantageously applied to a CAT or MRI bed (FIG. 1d). In this case, it is provided that the sensor means 4 and the light sources 3 inside the housing body 2 of the device are further housed in a shielding 11 of any suitable type, made, for example, of copper.

It will be observed that, due to the use of the deflector means 6 and the elongated configuration of the housing body 2 as well as the reduced size of the device 1, it is possible to insert the device 1 inside a magnetic resonance coil, maintaining the electrical components (the sensor means 4, the light sources 3, the reference means 5 and the data processing and control unit 9) far from the magnetic fields that can be generated therein.

The fact that the reference light source 5 is seen by the subject (during use), by reflection in the mirror 6a or in the mirror 7b, is also advantageous since it increases the distance of the fixation point form the patient and hence facilitates the stabilization of the gaze of the eye O under examination.

Also in order to make the device 1 according to the present invention compatible with the CAT and MRI equipment, the housing body 2 as well as the support means 8 are advantageously obtained in a metallic or polymer material characterized by low magnetic susceptibility and high resistance to ionizing radiations, e.g. made of aluminum or polyoxymethylene (POM). In order to avoid distortions on the images acquired with the MRI, suitable shielding and the use of radiofrequency filters are provided for the electrical power supply cables and the connection cables between the various components of the device.

The functioning of the device 1 according to the present invention described above is quite simple and reliable.

Figure 8:
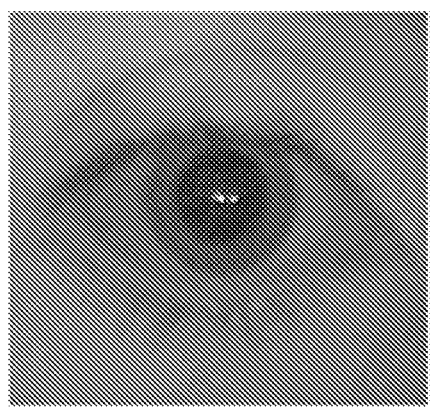
FIG. 8 illustrates the ocular region that is the object of measurement with the device according to the present invention.

In the following description, the device 1 is assumed to be equipped with the deflector means 6; it is given that the infrared light irradiation RL of the eye by the light sources 3 (or IR LEDs), arranged non-coaxially with respect to the optical axis of the telecameras, causes (in the eye O under examination) a dark pupil effect with high contrast and very bright corneal reflections (so-called glint), as shown in FIG. 8. The pupil and glint centers can be easily identified, in any one suitable manner, on the ocular images acquired by the sensor means 4, e.g. according to the analysis procedure described in "Robust algorithm for pupil-glint vector detection in a video-oculography eyetracking system", S. Goni, J. Echeto, A. Villanueva and R. Cabeza, *Proc. Int. Conf. on Pattern Recognition*, Cambridge, 2004, pp. 941-944.

Figure 3:
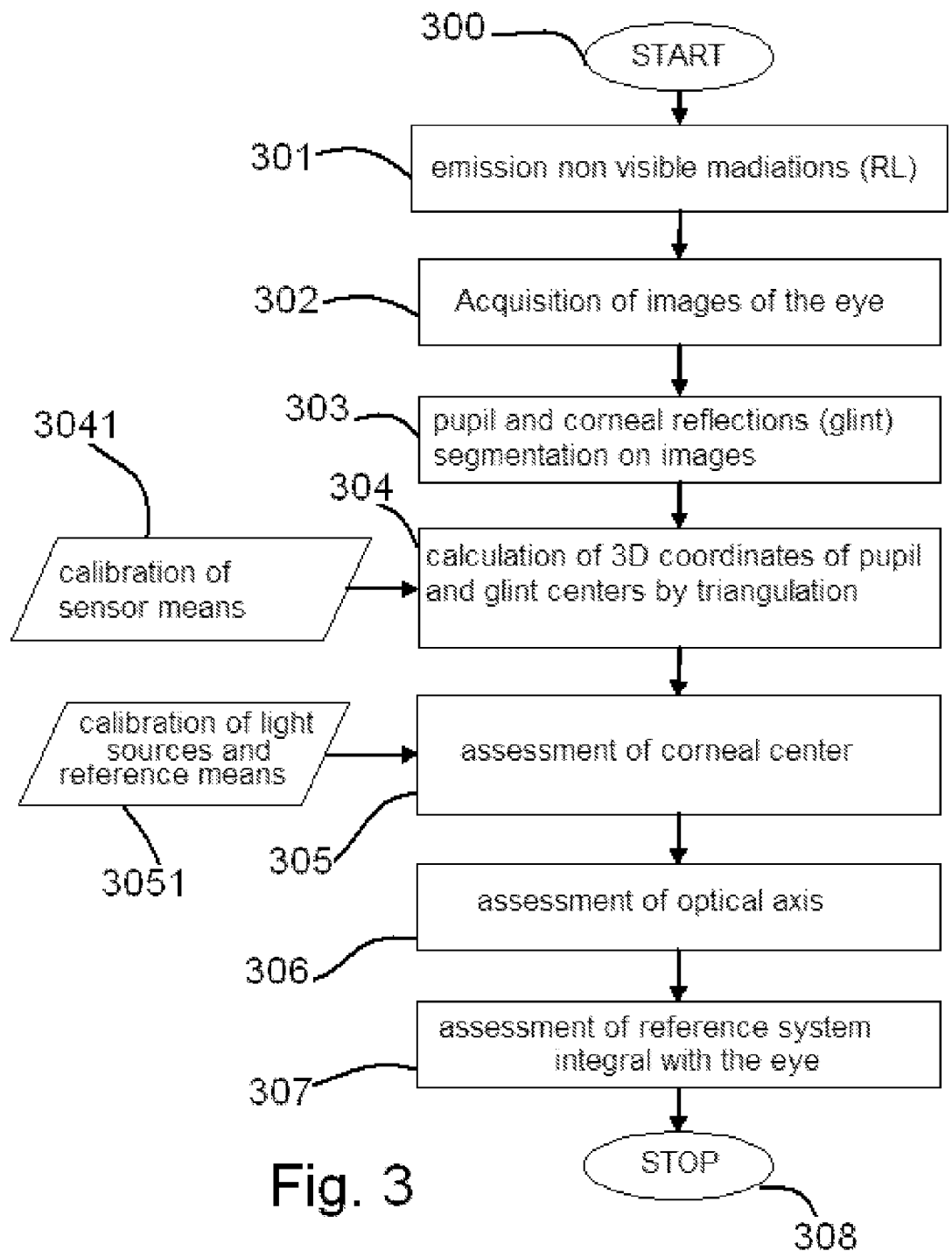
FIG. 3 is a flow diagram relative to the functioning of the device according to the present invention during the step of determination of a reference system integral with an eye under examination, with respect to a predetermined three-dimensional reference system.

The monitoring of the eye position and the ocular movements by means of the above-described device 1 comprises:
- a preliminary step in which the device 1 is arranged in a manner such that the through opening 2a of the housing body 2 is in correct correspondence with the eye O to be examined; and
- a subsequent procedure, with cyclic repetition, of estimating the ocular position and orientation according to the steps illustrated in FIG. 3.

The procedure for estimating the ocular position and orientation of FIG. 3 with respect to a predetermined three-dimensional reference system provides that, after an initial step 300, the data processing and control unit 9 sends a suitable electrical signal to the light sources 3, which, in response, emit infrared light RL which is thus directed towards the eye O under examination (step 301). In step 302, the data processing and control unit 9 activates the sensor means 4, which detect the infrared light reflected by the eye O and encode it into respective images, which are then sent to the data processing and control unit 9 set to process them.

The processing by the unit 9 comprises the estimation of the three-dimensional position and orientation of the eye O under examination, with respect to a predetermined three-dimensional reference system, starting from the identification of the pupil and corneal reflections on the images acquired and transmitted by the sensor means 4. Such images are processed by means of techniques of automatic segmentation of the glint and pupil centers (step 303), which techniques are based on operations of extraction of regions of interest, application of gray level thresholds, recognition and "fitting" of the borders. The identification on the images of the glint and pupil centers allows the reconstruction of the three-dimensional position (i.e. with respect to the predetermined three-dimensional reference system) of two points inside the eye O under examination, i.e. the center of the pupil, in step 304, and the center of the cornea (step 305); this is known from "General theory of remote gaze estimation using the pupil center and corneal reflections", by E. D. Guestrin and M. Eizenman, in *IEEE Trans. Biomed. Eng.*, vol. 53, pp. 1124-1133, June 2006.

Figure 7A:
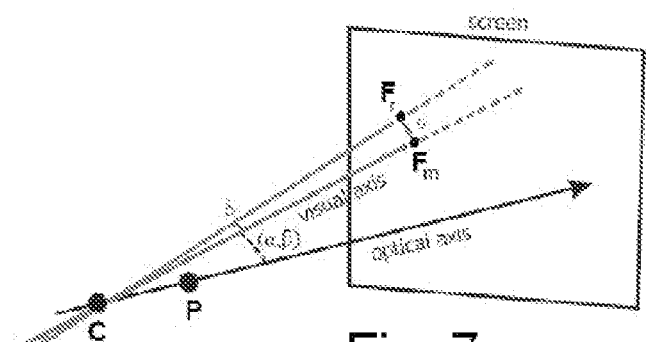
FIG. 7a schematically shows the optical axis and the gaze line of the eye with respect to the cornea and pupil centers.
Figure 7B:
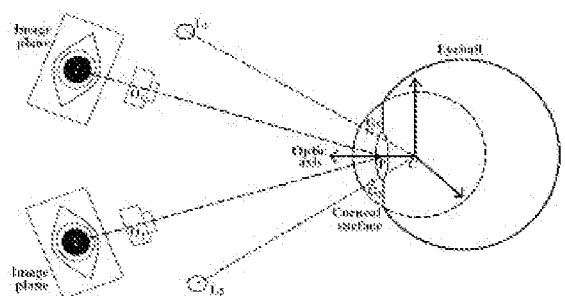
FIG. 7b is a schematic representation of an eye, in which the following are indicated: cornea C and pupil P centers, the corneal reflections G, the light sources L and the optical centers O of the sensor means.

More particularly, as schematically illustrated in FIG. 7b, the coordinates of the pupil center are obtained directly from triangulation of the respective projections on the sensor planes of the telecameras 4a and with the use of calibrated parameters (step 3041) of the same telecameras 4a, i.e. parameters which relate to the mutual position and orientation of the telecameras with respect to the predetermined three-dimensional reference system. The center of curvature of the cornea (step 305) is instead estimated as point of intersection between the lines joining the light sources 3, i.e. IR LEDs, with the generated corneal reflections.

Since the subject's eye O under examination is seen by the telecameras 4a through the reflection in the mirror 6a, it is necessary to place markers on the reflecting surface 6a in order to locate it in space, with respect to the predetermined three-dimensional reference system, and obtain the actual position of the corneal reflections on the eye O under examination, with respect to the predetermined three-dimensional reference system. The three-dimensional coordinates of the glint (p) are calculated starting from the respective reflections (r) in the mirror 6a and from the position of three passive markers applied on the reflecting surface, by using the following equation:

$$p = r - 2((r-q)^T n)n$$

where
q represents the barycenter of the markers
n is the normal to the mirror 6a.

Once the three-dimensional coordinates of the pupil and corneal center have been calculated with respect to the predetermined three-dimensional reference system, the orientation (with respect to such predetermined reference system) of the optical axis of the eye O under examination, i.e. the axis through the pupil and corneal centers, is estimated at step 306. At step 307, a reference system integral with the eye, as shown in FIG. 7b, is estimated, having as origin the center of the cornea and as anteroposterior axis of the eye O the optical axis joining the corneal and pupil centers. It will be noticed that the reference system integral with the eye under examination thereby calculated is referred with respect to the predetermined three-dimensional reference system.

According to the present invention, it is not necessary to calculate the mediolateral axis of the eye O, which can instead be considered as always belonging to the sagittal plane, since the torsion ocular movements are normally prevented in this type of application (due to the fact that the subject's head is usually immobilized with the aid of rigid thermoplastic head holders). The fact that the torsion movements of the eye are nearly negligible justifies the selection, for the support means 8, to be provided with 5 degrees of freedom instead of 6 degrees of freedom which are in theory normally requested.

As specified above and as can be observed in FIG. 3, the calculation of the position and orientation of the reference system integral with the eye, with respect to the predetermined three-dimensional reference system, requires specific calibration procedures that regard the stereoscopic telecameras (step 3041) and the light sources (step 3051), whose mutual position in the predetermined three-dimensional reference system must be known.

The calibration of the physical and geometrical parameters of the stereoscopic telecameras 4a (step 3041) with respect to the predetermined three-dimensional reference system, which allows correcting the optical distortions of the lenses and implementing three-dimensional triangulation techniques, is obtained by means of multiple views of a flat chessboard (not represented in the drawings). The calibration of the light sources 3 (step 3051), on the other hand, consists of the calculation of the three-dimensional position (i.e. with respect to the predetermined three-dimensional reference system) of the infrared LEDs and reference LEDs, which are rendered visible to the telecameras by using a mirror (not shown in the drawings) on which markers are applied in any one suitable manner. The three-dimensional coordinates of the light sources are calculated starting from the respective reflections in the mirror, by using the same equation above-reported for the estimation of the three-dimensional coordinates of the glint.

It will be observed that the above-described calibration procedures can be executed only once before the sensor means 4, the light sources 3 and the reference means 5 are assembled and anchored within the housing body 2 of the device 1, since those (as specified above) are rigidly anchored to each other even before their arrangement in the casing 2.

The device 1 according to the present invention can be advantageously integrated, as already indicated above, in the diagnostic equipment usually used for planning anti-tumor treatments for the eye, due to its specific structure which allows mounting it also on CAT and MRI beds.

The planning of the radiotherapy treatment of ocular tumors, as is known, is based on advanced techniques of acquiring and recording CAT and MRI images, which techniques allow defining the ocular region to be treated. On the CAT and MRI images thereby obtained, in addition to the zone of the eye to be treated, the critical ocular structures are also identified which are involved in visual functions (crystalline lens, macula and optical disc); such structures are considered for defining the safety margins of the target volume to be irradiated during treatment.

Figure 4:
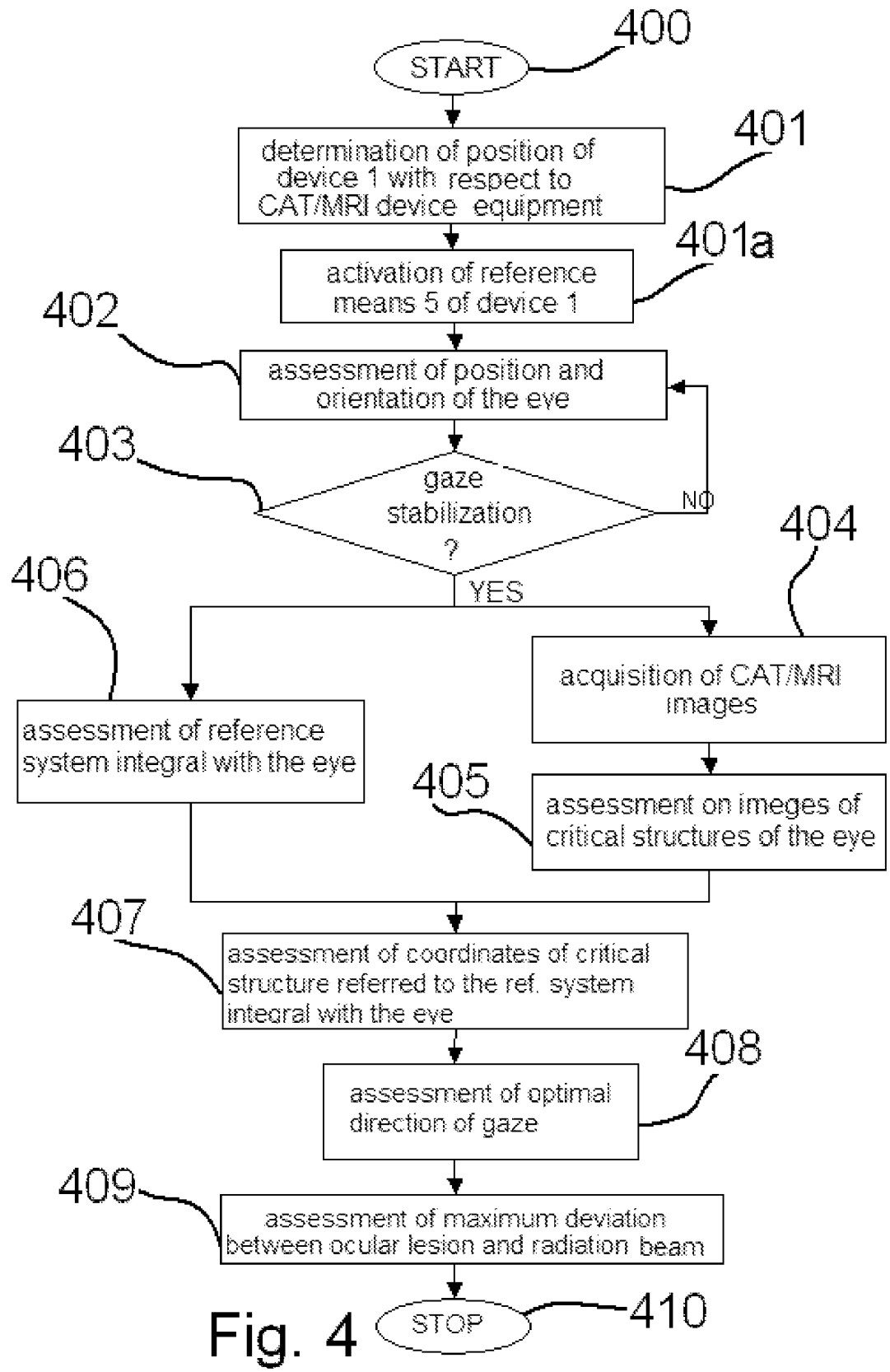
FIG. 4 illustrates a flow diagram which shows the step for planning a radiotherapy ocular treatment with the use of a device according to the present invention.

The device 1 according to the present invention can be advantageously employed in the planning step of an ocular treatment during the actual acquisition of the CAT/MRI images, as is illustrated in FIG. 4. Indeed, the device can be employed to establish if the gaze of a patient is stable (steps 402 and 403—in this case, one proceeds with the acquisition of CAT/MRI images in step 404) and to detect in real time the position of the eye (step 406) with respect to a predetermined three-dimensional reference system, such that a precise relation between each acquired CAT/MRI image and the respective position and orientation of the eye O at the time of image acquisition can established.

Gaze stabilization for a patient is obtained by having him/her staring at the reference means 5 of the device according to the present invention, which reference means is activated by the data processing and control unit 9 at step 410a.

Clearly, in order to be able to establish one such relation, a preliminary calibration step is necessary for the entire system, i.e. step 401, which will be executed only once at the time of the installation of the device 1 and, possibly, for periodic controls of the system. The step of preliminary calibration of the entire system is based on the anchorage of the device 1 at specific attachment points of the CAT/MRI bed provided for such a purpose (zone ZA illustrated in FIGS. 1c and 1d), by means of the use of the support means 8. Such anchorage or attachment points have known position with respect to the isocenter of the CAT/MRI system; therefore, by knowing the spatial arrangement or configuration of the support means 8 it is possible to associate the reference systems of the device 1 with the CAT/MRI systems. In this manner, one can establish the position of the device 1 according to the present invention with respect to the isocenter of the CAT/MRI system, and therefore, express the position of the isocenter of the CAT/MRI system, as well as that of device 1 according to the present invention, with respect to the predetermined three-dimensional reference system.

The stability of the gaze will be determined on the basis of suitable predefined reference thresholds and will be a necessary condition for the acquisition of the CAT/MRI images. More precisely, thresholds of 5°, typically employed in the treatments of stereotactic radiotherapy as indicated in B. Petersch, J. Bogner, K. Dieckmann, R. Pötter and D. Georga, "Automatic real-time surveillance of eye position and gating for stereotactic radiotherapy of uveal melanoma", *Med. Phys.*, vol. 31, pp. 3521-3527, December 2004, are considered acceptable.

The data acquired with the device 1 according to the present invention can be integrated with the CAT/MRI images, on which the critical ocular structures are identified (step 405); this in order to obtain an estimation of the coordinates of the ocular lesion, expressed in the reference system integral with the eye O under examination, determined by the device 1 (step 407).

Starting from this information, it is therefore possible establish the optimal direction that the gaze of the patient must follow during the actual treatment, so that the irradiation of the healthy ocular structures to be preserved is minimized (step 408), and the maximum tolerable deviations between the lesion and the radiation beam to be applied during eye treatment can be automatically determined (step 409). Such gaze direction and maximum tolerable deviations will be stored in the data processing and control unit 9 of the device according to the present invention.

More particularly, during the CAT and MRI acquisitions, the gaze direction of a patient is stabilized by asking the patient to gaze at the reference means 5 mounted in the device 1. As described above, the anchorage means 8a of the support means 8 are fixed to the medical bed in a calibrated position (ZA) with respect to the geometrical reference system of the CAT and MRI acquisition equipment. The arrangement of the support means 8 with respect to the medical bed is automatically set in an automatic and/or manual way such that the reference means 5 of the device 1 emits visible light which frontally hits the eye O.

During the planning of a treatment, as already specified above, it is possible to verify by means of the use of the device 1 according to the present invention the correct ocular position during the acquisition of the CAT and/or MRI images, by monitoring possible involuntary deviation of the gaze. The calibrated positioning of the device 1 with respect to the CAT and MRI acquisition systems also allows establishing the local coordinates of the lesion and the ocular structures at risk identified on the planning images, expressing them with respect to the reference system integral with the eye obtained by the device 1. In the specific case of proton therapy treatments, which are carried out by means of a single front beam, the planning of the treatment also allows optimizing the direction of the patient's gaze, which minimizes the radiation dose directed at the critical optical structures during treatment. In the case, however, of stereotactic radiotherapy based on the use of multiple irradiation fields, the direction of the gaze is set in the frontal rest position of the eye O in order to facilitate fixation.

The use of a device 1 for monitoring the position and the movements of the eye according to the present invention is also advantageous in the actual radiotherapy treatment step, in which it operates for:

verifying the correct positioning of the patient on the treatment chair or bed (and hence the correct positioning of its eye O to be treated); and sending of a feedback signal, to an operator supervising the treatment, on the position of the lesion with respect to the predetermined three-dimensional reference system.

In the case on involuntary movement of a patient, which movements could cause the radiation beam to hit healthy zones of the eye, such a feedback signal can be used by the operator to stop the administration of the radiation dose, the dose being supplied by an equipment for administration of the treatment dose, typically an accelerator of particles provided in a treatment room, which equipment for administration of the treatment dose does not form part of the present invention.

Figure 5:
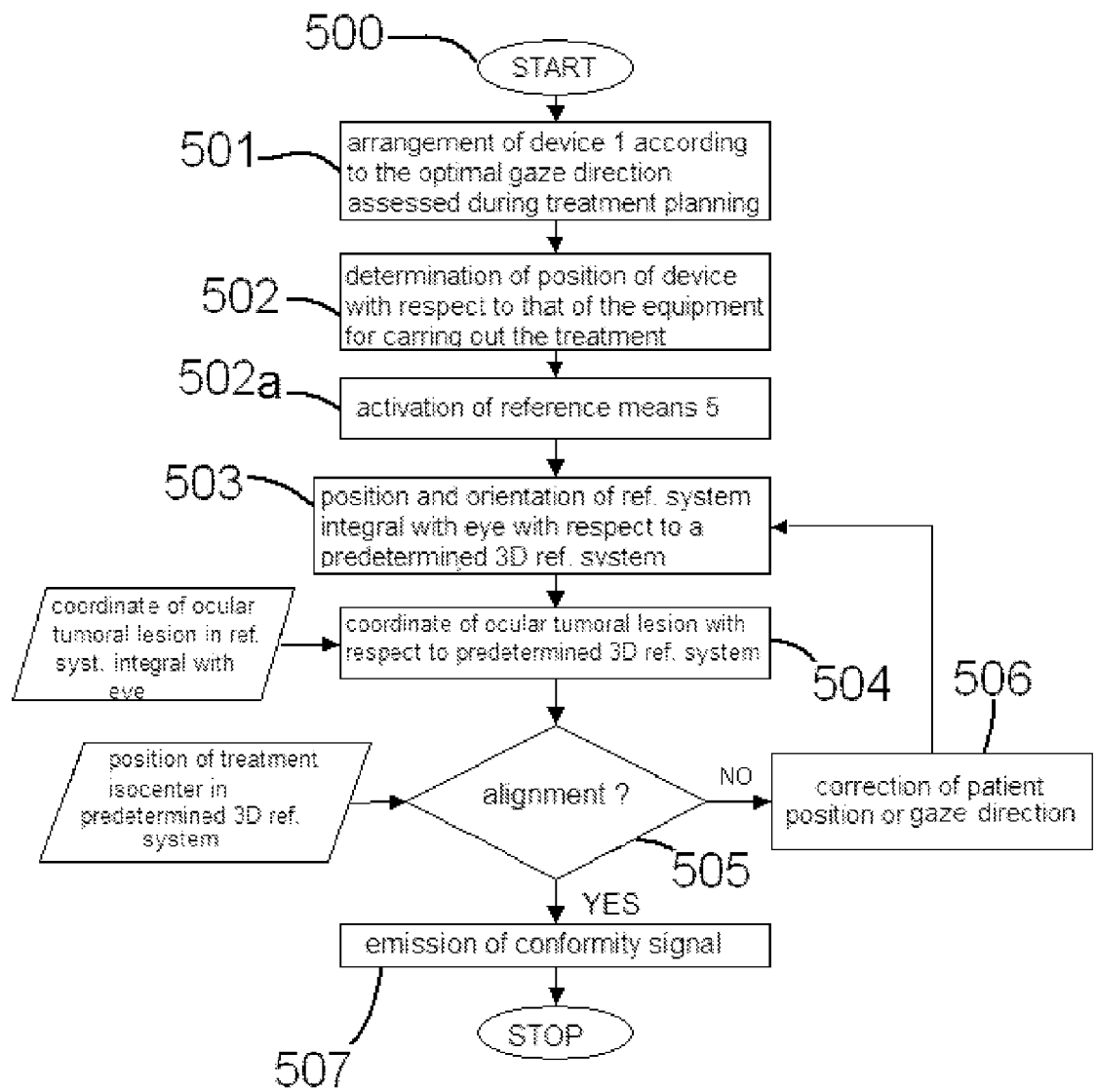
FIG. 5 shows a flow diagram which illustrates the step for positioning a patient before executing a treatment with the use of a device according to the present invention.

FIG. 5, in particular, shows a block diagram relative to the step of verification of the correct position of the patient before treatment. As it will be noted, at step 501, the device 1 according to the present invention is anchored to the medical bed in a calibrated point with respect to the radiation isocenter of the equipment for administration of the treatment dose; the device 1 is arranged, by means of the manual and/or automatic control of the position of the support means 8, in a manner such that the visible light emitted by the reference means 5 has a direction corresponding to the optimal direction of the gaze determined during the treatment planning (step 501). In treatments requiring the use of a motorized chair equipped with 7 degrees of freedom, generally rigidly connected to a thermoplastic mask in order to hold the head of a patient locked in position, the device 1 according to the present invention is anchored to the motorized chair (FIG. 1c) in a calibrated position with respect to the radiation isocenter; the device is adjusted, as in the case of the treatment bed, in a manner such that the visible light emitted by the reference means 5 has a direction corresponding to the optimal direction of the gaze determined during the planning of the treatment (step 501).

At the subsequent step, the position of the device 1 is correlated with the position of the equipment for administration of the treatment radiation dose (step 502), and once the reference means 5 of device 1 is activated at step 502a, which reference means 5 will be gazed by the eye O of the patient to be treated, a reference system integral with the eye O is reconstructed (step 503), which reference system allows localizing the tumor lesion and the ocular structures at risk during treatment step, in the case of invariance of the planned local coordinates (step 504).

At the subsequent step, step 505, and before each radiotherapy session, the alignment between the calibrated treatment isocenter and the position of the pathological volume or zone estimated with the device 1 is verified. In the case of possible positioning errors, at step 506 manual and/or automatic corrections to the translation and rotation parameters of the motorized chair or medical bed are determined, in order to obtain a correct alignment. If there are no position errors of the ocular lesion or pathological zone with respect to the predetermined reference system, the device 1 according to the present invention sends the operator a signal regarding the conformity of the position of the ocular lesion or pathological zone to be treated with respect to the treatment isocenter (step 507). Such a signal can be used by the operator in order to activate the equipment for administration of the treatment dose, the equipment administering the predetermined treatment dose.

Figure 6:
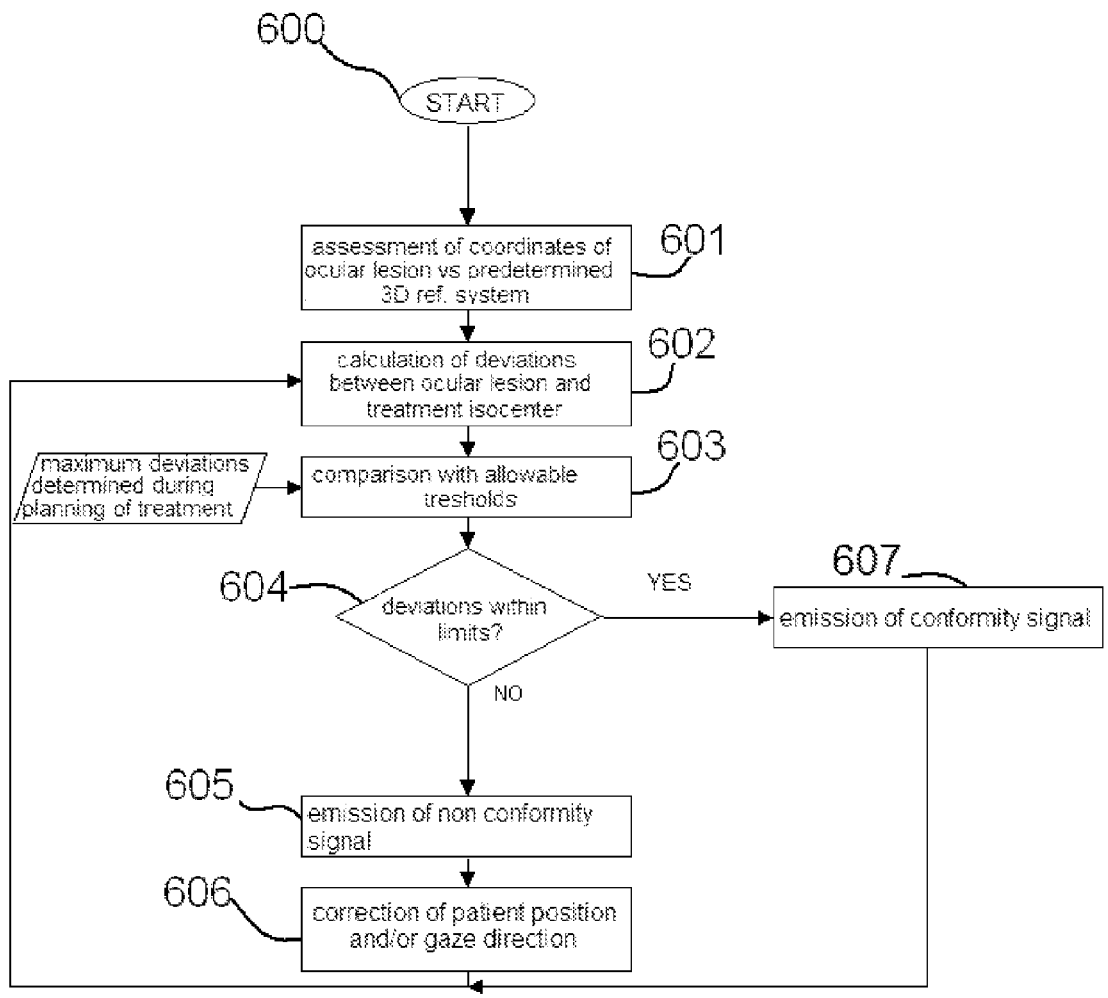
FIG. 6 is a flow diagram which shows a step for treating the eye by means of the use of a monitoring device according to the present invention.

The actual execution treatment step is illustrated in FIG. 6 and, during the release of the radiation dose by the equipment for administration of the treatment dose, it provides for, calculating, in real time, by the data processing and control unit 9 of the device 1 according to the present invention, the three-dimensional coordinates of the ocular lesion to be treated (step 601) with respect to a predetermined three-dimensional reference system, as well as the spatial deviations between the ocular lesion and the treatment isocenter (step 602) and comparing of the same (step 603) with the threshold values calculated in the treatment planning step (in step 409) in order to evaluate, at step 604, the entity of ocular movements.

It will be observed that the aforesaid threshold values are defined on the basis of the pathological volume or zone calculated during the planning of the treatment itself; hence, they are patient-specific and anisotropic, i.e. dependent on the rotation direction of the eye based on the vicinity of the ocular structures at risk.

If gaze deviations are detected which are greater than the preset threshold value, the device 1 according to the present invention will send a suitable signal regarding non conformity of the position of the pathological zone to be treated with respect to the treatment isocenter, step 605. If desired, the equipment for administration of the treatment dose can be programmed in order to stop automatically or manually (by the operator) the administration of the radiating dose, after device 1 has sent the non-conformity signal. At this point, the patient is notified and asked to correct the direction of the gaze (step 606) and the system recalculates the spatial deviation between the lesion or pathological zone and the treatment isocenter (step 602). If, at the following step 604, the system determines that the deviations are less than the allowed limits, the device 1 sends a new signal of conformity of the position of the pathological zone to be treated with respect to the treatment isocenter (step 607). If desired, the equipment for administration of the treatment dose can be programmed in order to reactivate automatically or manually (by the operator) the administration of the radiating dose. The control is then turned to step 602.

As will be observed, the device 1 according to the above-described present invention is advantageous in that it allows monitoring the position and the ocular movements, with respect to a predetermined reference system, in a non-invasive manner; it can also be personalized, in the sense that it is based on the ocular morphology of each single patient, and it is particularly easy and simple to use and advantageously employable in all the steps of planning and execution of the treatment. In addition, the automatic verification during treatment, by the device 1 according to the present invention, of the three-dimensional position of an ocular lesion or pathological zone with respect to the radiation isocenter (i.e. geometry conformity), as well as the output by the device 1 of a signal of conformity/non conformity of the position of the ocular lesion or pathological zone to be treated with respect to the treatment isocenter, allow the operator to stop the administration of treatment dose, for example when involuntary ocular movements of the patient occurs, and considerably reduces the risk of damaging healthy areas of the treated eye, thereby making the entire treatment safer and more reliable with respect to the systems employed up to now.

The device 1 according to the present invention is also precise and reliable, as is also inferred from practical tests for evaluating the accuracy of the ocular position and orientation, executed on a prototype of the device, object of the invention, and reported hereinbelow.

Due to the impossibility of directly measuring the actual coordinates of the cornea and pupil centers, the accuracy of device 1 according to the present invention was evaluating by following two indirect procedures, which measure the capacity of three-dimensional reconstruction, with respect to a predetermined three-dimensional reference system, of points in space and the estimation of the gaze direction.

Figure 10:
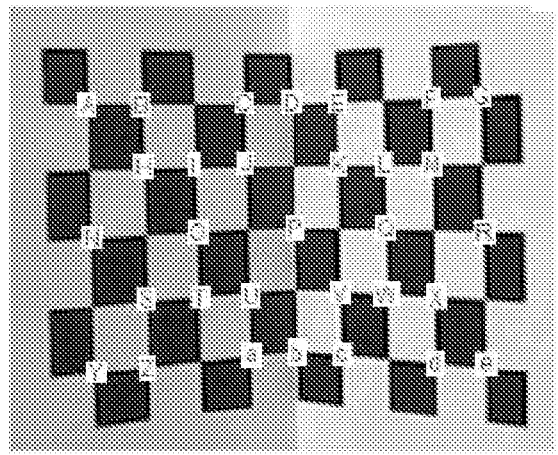
FIG. 10 shows a sample object used for executing the tests for the purpose of evaluating the precision and reliability of the device of the present invention.

With regard to the accuracy of device 1 in the 3D reconstruction, this was evaluated in reference to an error quantified by means of procedures taught in L. C. Silva, A. Petraglia and M. R. Petraglia, "A robust method for camera calibration and 3D reconstruction for stereo vision systems", in *Conf. EUSIPCO No.* 12, Vienna, 2004, pp. 1151-1154, which provide for the comparison of the actual and estimated distances between points that belong to a sample object (FIG. 10). The sample object used consisted of two chessboards, each composed of 30 squares (5×6) with 5 mm sides, the two chessboards brought together in a manner so as to delimit a right angle between them, for a total of 31 points of interest (see the letters reported on the chessboard of FIG. 10) and 18 segments with different lengths (HI, QW, AN, KM, Zb, FX, Ca, PR, OU, Lc, DS, TV, JM, BF, Ye, GH, Jd, EU) comprised between 5 and 30 mm.

From the geometric form and from the known size of the sample object, it was possible to find the length of the segments that connect the different points of the chessboard. The reconstruction error was then calculated on the basis of the differences between the known length of such segments and the measurement reconstructed through the device of the present invention.

By means of the triangulation function implemented by the device according to the present invention, the three-dimensional positions of the points of interest were calculated starting from the corresponding projections on the image planes of the telecameras. The estimated length of the segments of interest (L') was obtained by calculating the distance in space between two points (generically indicated as C1, C2) corresponding to the ends of each considered segment:

$$L' = \sqrt{(x_{C_1}-x_{C_2})^2+(y_{C_1}-y_{C_2})^2+(z_{C_1}-z_{C_2})^2}$$

The obtained values were compared with the corresponding actual lengths (L). For each segment of interest, the absolute error was then obtained ($E_A$), expressed in mm, given by the difference between the estimated length and the real length:

$$E_A = |L'-L|$$

In order to obtain an evaluation index independent of the size of the test object, the percentage relative error ($E_R$) was also calculated, by dividing the absolute error by the actual length of the corresponding segment:

$$E_R = \frac{|L'-L|}{L} \cdot 100$$

The calibration error, both absolute and relative referred to a specific view of the test object, can be obtained by carrying out the mean of the errors associated with the single segments of interest. In order to evaluate the dispersion of the error distribution around the mean value, the corresponding standard deviation was also calculated.

Such process was repeated for four views of the test object corresponding to different spatial positions and orientations of the chessboards. For each view, the distance of the object from the telecameras was also varied, within the interval of distances adapted for the prototype device. The mean value of the errors associated with the different views represents an indication of the accuracy of reconstruction of the three-dimensional position of points belonging to the possible work volume. In order to evaluate the repeatability of the obtained results, the test procedure was carried out for two different calibrations of the stereoscopic device 1 according to the present invention.

Table 1 reports the mean value and the standard deviation of the reconstruction errors for each test set. The overall value of the mean relative errors resulted less than 0.35%, corresponding to an absolute error of 0.05 mm, which can be considered acceptable for the estimated lengths. The absolute errors thus obtained did not result correlated to the length of the reconstructed segments, as shown by the value p of the Spearman test (p=0.13), whereas the positive and negative signs of the errors were uniformly distributed (Wilcoxon test, p=0.96). Systematic errors were therefore excluded; such errors can be related to incorrect calibration and triangulation techniques. The main error source was associable to random uncertainties, mainly due to imprecision in the extraction of the point projections starting from the acquired images.

TABLE 1

Accuracy results in the three-dimensional reconstruction tests

| | 1st Calibration Procedure | | 2nd Calibration Procedure | |
| --- | --- | --- | --- | --- |
| View | Absolute Error (mm) | Relative Error (%) | Absolute Error (mm) | Relative Error (%) |
| 1 | 0.037 ± 0.048 | 0.262 ± 0.334 | 0.043 ± 0.049 | 0.270 ± 0.294 |
| 2 | 0.041 ± 0.040 | 0.268 ± 0.223 | 0.044 ± 0.041 | 0.295 ± 0.234 |
| 3 | 0.043 ± 0.056 | 0.279 ± 0.348 | 0.052 ± 0.053 | 0.383 ± 0.391 |
| 4 | 0.038 ± 0.030 | 0.290 ± 0.266 | 0.052 ± 0.051 | 0.416 ± 0.537 |
| Total value | 0.039 ± 0.044 | 0.275 ± 0.291 | 0.048 ± 0.048 | 0.341 ± 0.379 |

Figure 9A:
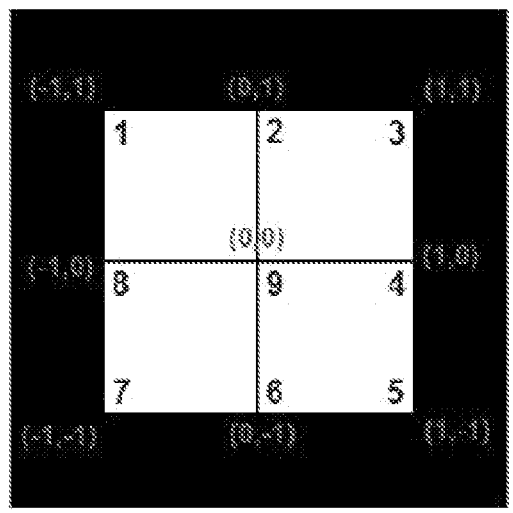
FIGS. 9a and 9b respectively illustrate a fixation grid used for executing the tests on the device according to the present invention and the distribution of the points gazed by a subject.
Figure 9B:
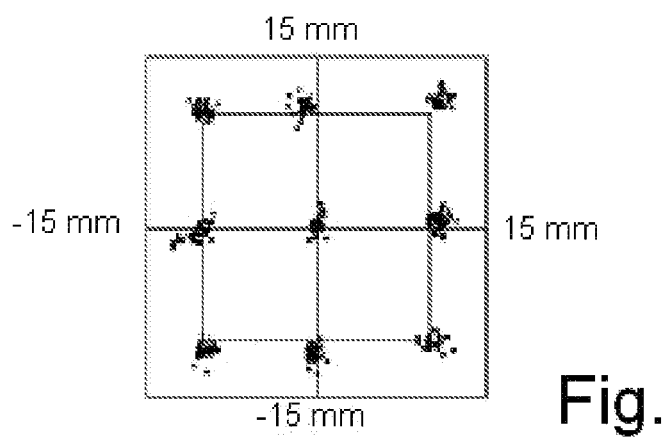

With regard to the evaluation of the gaze direction, the respective error was quantified over five (5) healthy subjects, by evaluating the eye preferred by such objects (both eyes were evaluated only for one subject). The evaluation of the gaze direction required, for each subject, a specific calibration of the angular deviations between the optical axis and the sight axis, which represents the gaze line joining the center of the cornea with the point fixated by the subject (FIG. 7a). The estimation accuracy of the gaze line was tested by making the subjects fixate up to 9 known coordinate points, represented by the vertices and by the mean points of the fixation grid (see FIG. 9a). For each point, the angular and spatial errors were measured by executing an average over 30 consecutive frames (images). The angular error (identified with δ in FIG. 7a) was calculated as the difference between the calculated orientation of the visual axis and the actual gaze direction, which connects a known fixation point with the center of curvature of the cornea identified according to the above-illustrated procedures. The spatial error in the calculation of the gaze direction (denominated with e in FIG. 7a) was calculated as the difference between the actual position of the fixation point and the coordinates of the gaze point estimated starting from the intersection of the visual axis reconstructed with the grid surface. In order to evaluate the reproducibility of the gaze accuracy results, two subjects repeated the test with different calibration procedures for the stereo telecameras and the light sources. Table 2 summarizes the statistical results relative to the mean accuracy of the measurement of the gaze direction calculated in each test set. The angular error resulted on average less than 1° for all the subjects tested, with a mean value equal to 0.53°. FIG. 9b shows the distribution around each vertex of the fixation grid of the estimated gaze points for a subject. It was established that the spatial estimation error for the gaze is proportional to the work distance between the eye and the fixated point, whereas the angular accuracy does not depend on the position of the eye with respect to the fixation grid.

TABLE 2

Results of the accuracy in the gaze direction estimation tests

| Session | Subject | Eye | Work distance (mm) | Spatial accuracy (mm) | Angular accuracy (°) |
| --- | --- | --- | --- | --- | --- |
| I | 1 | left | 128 | 1.16 ± 0.23 | 0.51 ± 0.09 |
| I | 1 | right | 129 | 1.24 ± 0.32 | 0.54 ± 0.12 |
| I | 2 | left | 119 | 0.98 ± 0.18 | 0.46 ± 0.09 |
| I | 3 | right | 129 | 1.38 ± 0.31 | 0.61 ± 0.13 |
| I | 4 | right | 134 | 1.44 ± 0.45 | 0.60 ± 0.17 |
| I | 5 | left | 127 | 1.10 ± 0.19 | 0.48 ± 0.08 |
| II | 1 | right | 175 | 1.60 ± 0.34 | 0.50 ± 0.11 |
| II | 2 | left | 168 | 1.56 ± 0.24 | 0.52 ± 0.08 |

Another fundamental aspect in the practical applications of the device that is the object of the present invention regards its high computational performances; these are indispensable, for example, during administration of the treatment dose when the data processing needs to be fast and the conformity or non-conformity signal must be promptly emitted by device 1, so that the operator can determine whether it is opportune to suspend the treatment following involuntary ocular movements of a patient.

Such computation performances were evaluated based on the execution time and on the number of clock cycles of the CPU associated with the functions of monitoring an eye under examination.

The information supplied by the number of cycles is particularly useful, since it does not depend on the clock frequency of the specific processor for the test procedure. The computational performance was evaluated on the same subjects who were also subjected to the other tests, using a 2.53 GHz Intel Core 2 Duo processor. With each acquired image, the time and the number of cycles of the CPU were calculated, associated with the process for monitoring the ocular movements; the mean values of the time and number of cycles were determined over 50 successive frames.

The results obtained for the different subjects are indicated in Table 3. The ocular monitoring frequencies attained with the implemented algorithm resulted on average equal to about 100 Hz. The observed variability between subjects can be associated with the individual difference in pupil diameter. In particular, the calculation time resulted linearly correlated with the size of the pupil, which determines the area of the region of the image that must be processed for the pupil center segmentation. The execution time of each of the eye monitoring steps was also estimated. It was determined that the image processing techniques for the identification of the pupil takes most of the computational load. A significant percentage of time is also associated with the acquisition and display of the ocular images in the user graphical interface.

TABLE 3

Results of the computational performance test

| Subject | Eye | Pupil size (pixels) | Clock cycles ($10^6$ cycles) | CPU time (ms) |
| --- | --- | --- | --- | --- |
| 1 | left | 53 | 27.595 ± 0.552 | 10.922 ± 0.219 |
| 1 | right | 50 | 27.202 ± 0.731 | 10.766 ± 0.289 |
| 2 | left | 25 | 23.808 ± 0.802 | 9.425 ± 0.317 |
| 3 | right | 50 | 27.421 ± 0.546 | 10.853 ± 0.216 |
| 4 | right | 19 | 23.289 ± 0.580 | 9.218 ± 0.227 |
| 5 | left | 24 | 23.949 ± 0.689 | 9.479 ± 0.273 |

The computational times, even if minimizable by employing particular technical design expedients, are compatible with a precise and reliable functioning of the device described above.

The above-reported analysis proves that the above-described device, in addition to being advantageously non-invasive and compatible with diagnostic instrumentation employing ionizing radiation and magnetic fields, is precise and reliable in the automatic evaluation of ocular position and movements both in diagnostic step and when administering the therapeutic treatment.

The above-described device for non-invasive monitoring the eye position and ocular movements is susceptible to numerous modifications and variations within the scope of protection defined by the following claims.

What is claimed is:
1. A device for non-invasive monitoring of the position and ocular movements of an eye of a patient, comprising:
   a housing body having at least one through opening;
   a plurality of light sources located in said housing body and suitable for emitting invisible radiation through said at least one through opening;
   a plurality of sensor means housed in said housing body and secured thereto and to said plurality of light sources, said plurality of sensor means being designed to
      detect said invisible radiation emitted, in use, by said plurality of light sources outside said housing body and reflected by the eye under examination, and
      convert said detected invisible radiation into a suitable electrical signal;
   deflector means for said invisible radiation emitted, in use, by said plurality of light sources and reflected by said eye under examination, the deflector means being supported by said housing body at said at least one through opening;
   adjustable support means for said housing body;
   at least one program data processing and control unit electrically connected to said plurality of light sources, to said plurality of sensor means and to said support means, and designed to send/receive suitable control signals to/from said plurality of light sources, to/from said plurality of sensor means and to/from said support means and to process said electrical signal correlated with the invisible radiation detected by said plurality of sensor means,
   wherein
   said support means are adjustable in such a way that said through opening of said housing body is placeable at said eye under examination whereby said invisible radiation hit said eye frontally and the at least one program data processing and control unit is designed to calculate instant-by-instant the position and orientation of a suitable three-dimensional reference system inte- gral with the eye, with respect to a predetermined three-dimensional reference system.

2. A device according to claim 1 wherein said adjustable support means comprise a robotic manipulator having at least five degrees of freedom.

3. A device according to claim 2, wherein said robotic manipulator is anchorable to a treatment bed or chair in a known position with respect to an equipment for planning and/or administering a therapeutic treatment.

4. A device according to claim 1, wherein said plurality of light sources comprise at least one couple of infra-red LEDs.

5. A device according to claim 1, wherein said plurality of sensor means comprise at least a couple of high spatial and temporal resolution miniaturized stereoscopic telecameras responsive to invisible radiation emitted by said plurality of light sources and reflected by said eye under examination.

6. A device according to claim 1, further comprising a reference means located in said housing body and suitable for emitting visible radiation through said through opening.

7. A device according to claim 6, wherein said visible radiation emitted by said reference means is transmitted by said deflector means to said eye.

8. A device according to claim 7, wherein said reference means comprises a visible light LED.

9. A device according to claim 8, wherein said deflector means for said invisible radiation and for said visible radiation emitted by said reference means comprise at least one mirror arranged at said through opening in said housing body according to an angle such that said invisible radiations emitted by said plurality of light sources and said visible radiation emitted by said reference means and transmitted by said mirror hit frontally said eye under examination.

10. A device according to claim 6, comprising auxiliary deflector means for the visible radiation emitted by said reference means.

11. A device according to claim 10 wherein:
said housing body has at least one auxiliary through opening for the outlet of said visible light emitted by said reference means from said housing body; and
said auxiliary deflector means comprise at least a first mirror and a second mirror externally anchored to said housing body,
said first mirror being provided at said auxiliary through opening in order to transmit the visible light emitted by said reference means towards said second mirror, said second mirror being designed to transmit said visible light transmitted by said first mirror towards the eye not being under examination.

12. A device according to claim 1, wherein said data processing and control unit is electrically connected to input-output means.

13. A device according to claim 12, wherein said input-output means are connectable to an equipment for planning a therapeutic treatment and/or an equipment for carrying out said therapeutic treatment.

14. A device according to claim 6, comprising a shielding housing said plurality of light sources, said plurality of sensor means, and said reference means.

15. A device according to claim 1, wherein said housing body and said support means are made of a material having a low magnetic susceptibility and high resistance to ionizing radiations.

16. A device according to claim 6, wherein said housing body is dimensioned such that said plurality of light sources, said sensor means and said reference means are mounted therein at sufficient distance with respect to said through opening, whereby, when said device is combined with an equipment for acquisition of CAT/MRI images or for administration of a treatment dose, said plurality of light sources, said sensor means and said reference means are outside the range of said devices affected by magnetic fields and/or radiations.

17. A method of non-invasive monitoring of the position of an eye and of ocular movements of a patient, with respect to a predetermined three-dimensional reference system, comprising the following operative stages:
arranging a device according to claim 1 so that the invisible radiations delivered by said plurality of light sources frontally hit, in use, an eye to be examined;
emitting said invisible radiations towards said eye;
acquiring of at least a plurality of images encoded in suitable electrical signals by means of said data processing and control unit;
processing said electric signals by said data processing and control unit; and
calculating, on the base of said processing by said data processing and control unit, the position and orientation of a reference system integral with said eye under examination with respect to said predetermined three-dimensional reference system.

18. A method according to claim 17, wherein said step of processing electric signals by said data processing and control unit comprises the steps of:
automatic segmentation of the centers of pupil and cornea on said plurality of images encoded in said suitable electrical signals;
assessment of the position of the pupil center with respect to said predetermined three-dimensional reference system;
assessment of the position of the cornea center with respect to said predetermined three-dimensional reference system;
calculation of the optical axis passing through the pupil and cornea centers; and
calculus, on the base of the position of the cornea center and the optical axis thereby calculated, of the position and orientation of a reference system integral with the eye, with respect tot said predetermined three-dimensional reference system.

19. A method according to claim 17, wherein said data processing comprises the assessment of physical and geometrical parameters of said plurality of sensor means and of said plurality of light sources and said reference means with respect to said predetermined three-dimensional reference system.

20. A method according to claim 19, wherein said assessment of physical and geometrical parameters of said plurality of sensor means and of said plurality of light sources and said reference means with respect tot said predetermined three-dimensional reference system is performed only once, before said plurality of sensor means, said plurality of light sources, and said reference means are assembled in said housing body.

21. A method according to claim 17, when applied to planning a radiotherapy treatment of an eye by means of said device, wherein said device further comprises a reference means located in said housing body and suitable for emitting visible radiation through said through opening, wherein the method comprises the following steps in sequence:
arranging said device in a known position with respect to an equipment for acquisition of CAT/MRI images;
activating said reference means of said device, which the patient is invited to look at;

calculating of the position and orientation of said reference system integral with said eye, with respect to said predetermined three-dimensional reference system, according to claim 17;

if the orientation of said reference system integral with said eye is stable, acquiring morphological CAT/MRI images of said eye by means of said equipment for acquisition of CAT/MRI images, and assessing of healthy and pathological structures of said eye;

determining said reference system integral to said eye;

calculating of the coordinates of any healthy and pathological structures of said eye referred to said reference system integral to said eye;

calculating of the optimal gaze direction of said eye with respect to said predetermined three-dimensional reference system, which direction minimizes the probability of treating healthy ocular structures; and definition, based on the calculations thereby performed, of maximum acceptable deviations between pathological structures to be treated and treatment beam.

22. A method according to claim 21, when positioning before treatment a patient onto a treatment bed or chair with said device, said method comprising the following steps in sequence:

positioning said device in a known relation with respect to said treatment bed or chair and with respect to said equipment for administering said treatment dose, said equipment for administering said treatment dose having a treatment isocenter, whereby said reference means of said device is at said optimal gaze direction of said eye of a patient, said optimal gaze being calculated during said treatment planning;

calculation of the position of said device with respect to said equipment for administering said treatment dose;

activation of said reference means of said device which the patient is invited to look at;

assessment of the position and orientation of said reference system integral to said eye, with respect to said predetermined three-dimensional reference system;

calculation of the three-dimensional coordinates of said pathological zone of said eye to be treated, with respect to said predetermined three-dimensional reference system;

checking the alignment, in said predetermined three-dimensional reference system, between said treatment isocenter of said equipment for administering said treatment dose and said pathological zone to be treated;

if alignment occurs, emission of a conformity signal;

if alignment does not occurs, correction of the position of said patient and/or of the direction of his gaze.

23. A method according to claim 22, wherein said step of correction of the position of said patient and/or of the his gaze direction requires the look of said reference means of said device by said patient.

24. A method according to claim 22, for assessing, by means of said device for non-invasive monitoring of the eye position and of ocular movements, if a treatment dose, administered by an equipment for administering a treatment dose, hits the zone to be treated of said eye, said method comprising the following steps in sequence:

calculating the three dimensional coordinates, with respect to said predetermined three-dimensional reference system, of a pathological zone of said eye;

calculating the deviations between said pathological zone of said eye and said treatment isocenter of said equipment for administering said treatment dose;

comparing said deviations thereby calculated with allowable threshold values stored in said data processing and control data of said device;

if said deviations exceed said threshold values, emission of a nonconformity signal of the position of the pathological zone to be treated with respect to said treatment isocenter;

positioning again said pathological zone to be treated of said eye at said treatment isocenter of said equipment for administering said treatment dose;

calculating again said deviations between said treatment isocenter and said pathological zone to be treated;

comparing said deviations thereby calculated with allowable threshold values; and if said deviations do not exceed said threshold values, emission of a conformity signal of the position of said pathological zone to be treated with respect to said treatment isocenter.

* * * * *